United States Patent [19]

Oftebro et al.

[11] Patent Number: 5,130,145

[45] Date of Patent: Jul. 14, 1992

[54] PHARMACEUTICAL COMPOSITIONS WITH ANIT-CANCER ACTIVITY AND METHOD FOR THE TREATMENT OF CANCER

[75] Inventors: Reidar Oftebro, Hvalstad; Erik O. Pettersen; John M. Dornish, both of Oslo; Bernt Borretzen; Rolf O. Larsen, both of Porsgrunn, all of Norway

[73] Assignee: Norsk Hydro A.S., Oslo, Norway

[21] Appl. No.: 718,363

[22] Filed: Jun. 20, 1991

Related U.S. Application Data

[62] Division of Ser. No. 329,379, Mar. 27, 1989, Pat. No. 5;049,396.

[30] Foreign Application Priority Data

Apr. 29, 1988 [GB] United Kingdom ............... 8810173

[51] Int. Cl.$^5$ .................. A61K 33/24; A61K 31/335
[52] U.S. Cl. .................................... 424/649; 514/467
[58] Field of Search ....................... 514/467; 424/649

[56] References Cited

FOREIGN PATENT DOCUMENTS 0148094 7/1985 European Pat. Off. ............ 514/467

OTHER PUBLICATIONS

See-Lasley et al., Manual of Oncology & Jerapeutics, 1981, pp. 189–190.
Carter et al., Chemotherapy of Cancer, 2nd Ed. 1981, pp. 107–108.
Zaizen et al., J. Cancer Research Clin. Oncol. (1986) III, pp. 93–97.
Nechay et al., Cancer Treat. Rep., vol. 68, No. 9 Sep., 1984, pp. 1135–1141.

Primary Examiner—Jerome D. Goldberg
Attorney, Agent, or Firm—Wenderoth, Lind & Ponack

[57] ABSTRACT

Anti-cancer platinum complexes such as cisplatin exhibit a synergistically higher level of anti-tumour activity when administered substantially simultaneously either with L-ascorbic acid, or with 5,6-O-benzylidene-L-ascorbic acid or deuterated forms thereof.

9 Claims, No Drawings

PHARMACEUTICAL COMPOSITIONS WITH ANIT-CANCER ACTIVITY AND METHOD FOR THE TREATMENT OF CANCER

This application is a division of application Ser. No. 329,379, filed Mar. 27, 1989 (now U.S. Pat. No. 5,049,396).

BACKGROUND OF THE INVENTION

This invention relates to pharmaceutical compositions which have activity as anti-cancer agents and to methods for the treatment of cancer in patients.

Cisplatin, or cis-dichlorodiammineplatinum-II, has been used successfully for many years as a chemotherapeutic agent in the treatment of various human solid malignant tumours. Cisplatin has the structural formula:

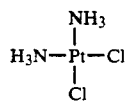

More recently, other diamino-platinum complexes have also been proposed for use as anti-cancer drugs, for example spiro-platinum and carbo-platinum.

Although cisplatin is widely used in medicine, nonetheless it is not therapeutically effective in all patients, nor against all types of solid malignant tumours. Moreover, it has to be administered at high dosage levels such as can cause kidney damage unless special precautions are taken.

SUMMARY OF THE INVENTION

It has now been found in accordance with the present invention that anti-cancer platinum complexes such as cisplatin unexpectedly exhibit a higher level of anti-tumour activity, as demonstrated by an in-vitro model, if administered substantially simultaneously either with L-ascorbic acid or with 5,6-0-benzylidene-L-ascorbic acid (hereafter sometimes abbreviated as BASS).

Although both L-ascorbic acid and BASS are disclosed in the literature as possessing anti-cancer properties, we have found that the enhancement of cytotoxic activity on human cancer cells which is exhibited when these substances are administered in conjunction with anti-cancer platinum complexes such as cisplatin is synergistic and not merely additive. This result is highly surprising, more especially since one effect of the co-administration of an anti-cancer platinum complex such as cisplatin with L-ascorbic acid or BASS is to reduce the up-take of platinum by the malignant cells, whereas the prior work on cisplatin in particular has taught that an increase in the platinum take-up increases the toxicity of cisplatin.

This synergism between cisplatin and L-ascorbic acid or BASS which we have discovered opens up the possibility of more effective cisplatin therapy and/or the use of lower dosages of cisplatin for reduced adverse toxic side-effects on the patient.

The L-ascorbic acid and 5,6-O-benzylidene-L-ascorbic acid (i.e. BASS) can be used herein either as free acids or in the form of their salts with pharmaceutically acceptable cations. Moreover, the 5,6-O-benzylidene-L-ascorbic acid may be deuterated at the 1-position of the benzylidene moiety; other work which we have done suggests that such deuterated BASS may have advantages in anti-cancer therapy over non-deuterated BASS.

Thus, in accordance with one aspect, the present invention provides a pharmaceutical composition useful as an anti-cancer agent, comprising as active ingredients:

(a) an anti-cancer platinum complex, and (b) a compound selected from L-ascorbic acid, 5,6-O-benzylidene-L-ascorbic acid, 5,6-O-benzylidene-L-ascorbic acid deuterated at the 1-position of the aldehyde group, and pharmaceutically acceptable salts of said acids.

The present invention also encompasses the use of a compound selected from L-ascorbic acid, 5,6-O-benzylidene-L-ascorbic acid, 5,6-O-benzylidene-L-ascorbic acid deuterated at the 1-position of the aldehyde group, and pharmaceutically acceptable salts of said acids, for the manufacture of a medicament for use in a platinum complex anti-cancer therapy.

Still further, the present invention provides a method for the treatment of cancer in a patient, which comprises simultaneously administering to said patient:

(i) an anti-cancer platinum complex, and (ii) a compound selected from L-ascorbic acid, 5,6-O-benzylidene-L-ascorbic acid, 5,6-O-benzylidene-L-ascorbic acid deuterated at the 1-position of the aldehyde group, and pharmaceutically acceptable salts of said acids. When referring herein to the treatment of cancer, Applicants are referring to the treatment of cancer sensitive to treatment with the compositions of the present invention.

It is preferred in accordance with this invention to use cisplatin as the anti-cancer platinum complex, and as the potentiating agent therefor, BASS or deuterated BASS.

The deuterated 5,6-O-benzylidene-L-ascorbic acid useful herein may additionally be partially or completely deuterated at other positions of its molecular structure, i.e., in addition to the deuterium atom at the 1-position of the aldehyde group of the benzylidene moiety, one or more hydrogen atoms in the structure may be replaced by deuterium atoms.

The pharmaceutical composition of this invention preferably comprises a freeze-dried mixture of the active ingredients in a unit dosage form ready for make-up with water for injection or other suitable infusion liquid. As is conventional with presently available freeze-dried formulations of cisplatin, the freeze-dried compositions of this invention may also include sodium chloride (to provide the required isotonicity to the infusion liquid), and/or mannitol (to help protect against kidney damage).

DETAILED DESCRIPTION OF THE INVENTION

The synergistic anti-cancer effect on which the present invention is predicated is demonstrated by the experiments described below. In these experiments there were used L-ascorbic acid or the sodium salt of 5,6-O-benzylidene-L-ascorbic acid (abbreviated as "BASS").

BIOLOGICAL MATERIALS AND METHODS USED TO DEMONSTRATE THE SYNERGISTIC EFFECT

Cell Culturing Techniques

Human cells of the established cell line NHIK 3025 originating from a cervical carcinoma in situ (Nordbye, K., and Oftebro, R. Exp. Cell Res., 58:458, 1969), Oftebro, R., and Nordbye, K., Exp. Cell Res., 58:459–460, 1969) were cultivated in Medium E2a (Puck, T. T. et al., J. Exp. Med., 106:145–165, 1957) supplemented with 20% human and 10% horse serum (Grand Island Biological Co.). The cells are grown as monolayers in tissue culture flasks. The cells do not move around after they have attached, a quality which enables the same cells to be observed in an inverted microscope for several cell generations. The cells were kept in continuous exponential growth by frequent reculturing, i.e., every second and third day.

Cell Survival

For measurement of cell survival, appropriate numbers of cells were seeded in plastic Petri dishes ($\phi=5$ cm). The number of cells seeded into each dish was adjusted such that the number of surviving cells would be approximately 150 per dish. While exponentially growing (asynchronous) cells were trypsinized before seeding, synchronized cells were seeded immediately after selection. After about 2 hours, the cells had attached to the bottom of the dishes, and the treatment was started by replacing the medium with medium containing the appropriate drug concentration. After the desired time of treatment, the drug-containing medium was removed, and fresh medium was added. The dishes were rinsed once with the same medium as was to be added on addition or removal of drug. After 10 to 12 days at 37° C. in a $CO_2$ incubator, the cells were fixed in ethanol and stained with methylene blue before the colonies were counted.

Duration of Cell Cycle Time

Synchronized cell populations with a high degree of synchrony were obtained by repeated selection of mitotic cells (Pettersen, E. O. et al, Cell Tissue Kinet., 10: 511–522, 1977). During the synchronization procedure, the cells were kept in Medium E2a, and the whole experiment took place in a walk-in incubator at 37° C. Under growth conditions as used here, the NHIK 3025 cells have a medium cell-cycle time of $\sim 18$ hr, with medium $G_1$, $S_1$ and $G_2$ durations of $\sim 7$, $\sim 8$, and $\sim 2.5$ hr, respectively.

For detection of the drug effects on cell-cycle kinetics, the same methods were used as described previously (Lindmo, T., and Pettersen, E. O., Cell Tissue Kinet., 12:43–57 1979), (Pettersen, E.O. et al, Eur. J. Cancer Clin. Oncol., 19:507–514, 1983), (Rønning, Ø.W. et al., J. Cell. Physiol., 109:411–419, 1981). Briefly, the selected mitotic cells were seeded into 8 tissue culture flasks (25 sq cm) 5000 cells per flask. The cells divided within 1 hr and attached as doublets to the bottom of the flasks. The cells within a delineated area of the flask (100 cells) were observed repeatedly in an inverted microscope, and the time of entrance into mitosis, as well as the time of division, were noted for each separate cell. Analyses of durations of mitosis were performed from these observations (Table).

Atomic Absorption Spectroscopy

Analysis of cell-associated platinum was performed using a Varian SpectrAA-30 atomic absorption spectrometer fitted with a GTA-96 graphite tube atomizer. Instrument control and data acquisition were by Varian Atomic Absorption Software. Automatic background correction with a modulated deuterium lamp was utilized. Cells were loosed from flasks by trypsin treatment and counted. Cells ($2 \times 10^6$) were added to conical centrifuge tubes, three replicate tubes for each drug concentration. The tubes were centrifuged and cells were resuspended in drug-containing medium, usually 3 ml/tube. The cells were incubated with drugs at 37° C. and held in suspension by using a rotary rack. After treatment the cells were centrifuged and washed in phosphate-buffered NaCl solution (NaCl, 8000 mg/liter; $Na_2HPO_4.2H_2O$, 1150 mg/liter; $KH_2PO_4$, 200 mg/liter; KCl, 200 mg/liter). The cell pellet was taken up into 100 µl concentrated $HNO_3$. Following overnight oxidation of organic material, 100 µl $H_2O$ was then added to each tube. Aliquots of 25 µl (representing 250,000 cells) were then placed in a graphite tube and the atomic absorption signal measured at 265.9 nm was registered. Platinum content was quantitated by running a calibration curve immediately before the samples.

EXPERIMENT 1

In this experiment, the fraction of growing NHIK 3025 cells surviving a two hour treatment with either 3 µM or 10 µM of cisplatin alone or in combination with various concentrations of BASS was measured. The results obtained are reported in Table 1 below:

TABLE 1

| Concentration of BASS (mM) | No Cisplatin | Fraction of Cells Surviving Treatment with Bass either alone or in combination with cisplatin: | |
|---|---|---|---|
| | | 3 µM cisplatin | 10 µM cisplatin |
| 0 | 1.0 | 0.39 ± 0.03 | 0.024 ± 0.01 |
| 2 | 1.06 ± 0.10 | 0.16 ± 0.01 | 0.0035 ± 0.0003 |
| 4 | 1.03 ± 0.06 | 0.16 ± 0.01 | 0.0026 ± 0.0003 |
| 10 | 0.79 ± 0.04 | 0.18 ± 0.01 | 0.0049 ± 0.0003 |

From the results shown in Table 1 it will be noted that the use of BASS at all three concentrations tested significantly potentiated the activity of the cisplatin. A BASS concentration of 4 mM can be seen to be slightly more effective than one of 10 mM.

EXPERIMENT 2

This experiment measured the fraction of NHIK 3025 cells surviving a 2 hour treatment with a combination of 3 µM cisplatin and either BASS or ascorbic acid, at various concentrations. The results are given in Table 2. The values given in the Table represent cell survival after the treatment with drug combination relative to that after treatment with 3 µm cisplatin alone.

TABLE 2

| Concentration of BASS or Ascorbic Acid (mM) | BASS + 3 µM cisplatin | Ascorbic Acid + 3 µM cisplatin |
|---|---|---|
| 0 | 1.0 | 1.0 |
| 0.25 | 0.92 ± 0.04 | 0.92 ± 0.06 |
| 0.5 | 0.95 ± 0.05 | 1.0 ± 0.05 |
| 1 | 0.56 ± 0.03 | 0.69 ± 0.04 |
| 2 | 0.42 ± 0.03 | 0.37 ± 0.03 |

Table 2 shows relative survival values i.e. relative to cisplatin alone, i.e. any potentiation of cisplatin toxicity by BASS or ascorbic acid would thus reduce the relative survival values to below 1.0. From Table 2, it will be seen that the potentiating effect of BASS and ascorbic acid on cisplatin were similar, but most apparent at concentrations above 0.5 mM.

EXPERIMENT 3

This experiment measured the fraction of NHIK 3025 cells surviving a 2 hour treatment with various concentrations of cisplatin either alone or in simultaneous combination with 1 mM of BASS. The results obtained are given in Table 3.

TABLE 3

| Cisplatin Concentration ($\mu$M) | Fraction of Surviving Cells: | |
| --- | --- | --- |
| | cisplatin alone | cisplatin + 1 mM BASS |
| 0 | 1.0 | 0.95 ± 0.05 |
| 1 | 0.98 ± 0.06 | 0.81 ± 0.05 |
| 2.5 | 0.70 ± 0.03 | 0.38 ± 0.02 |
| 5 | 0.24 ± 0.02 | 0.066 ± 0.003 |
| 10 | 0.018 ± 0.002 | 0.0079 ± 0.0006 |
| 25 | 0.00026 ± 0.00009 | 0.000029 ± 0.00001 |

From Table 3 it is seen that as the concentration of cisplatin increased, so did the effectiveness of the applied combination in killing the NHIK 3025 cells.

EXPERIMENT 4

This experiment was designed to test whether the synergistic effects were dependent on when the two drugs (i.e. BASS and cisplatin) were applied to the growing NHIK 3025 cells.

In Table 4 below, the values reported represent the fraction of cells surviving either treatment with 10 $\mu$M cisplatin alone, 2.5 mM BASS alone or treatment with the two drugs in combination. The combined treatment was given either by adding the two drugs simultaneously (0 hours) or adding BASS 1 hr, 2 hrs, 3 hrs or 4 hrs after addition of cisplatin. In all cases each individual drug was removed 2 hrs after it was added to the cells.

TABLE 4

| Drug treatment | Hours After Start of Cisplatin Treatment | | | | |
| --- | --- | --- | --- | --- | --- |
| | 0 | 1 | 2 | 3 | 4 |
| 2.5 mM BASS alone | 0.94 ± 0.09 | | | | |
| 10 $\mu$M cisplatin alone | 0.0062 ± 0.0005 | | | | |
| 10 $\mu$M cisplatin + 2.5 mM BASS | 0.00043 ± 0.00002 | 0.003 ± 0.0005 | 0.0069 ± 0.0005 | 0.0074 ± 0.0005 | 0.0053 ± 0.0005 |

From Table 4 it is seen that there was an approximately 10-fold enhancement of potentiation of cisplatin when cisplatin and BASS were added simultaneously as compared to when BASS was added at an interval following the addition of cisplatin.

EXPERIMENT 5

This experiment measured the prolongation of the median cell-cycle duration of synchronized cells treated with either 1.5 $\mu$M of cisplatin or 2.0 mM of BASS alone, or with the two active ingredients in simultaneous combination.

The results are given in Table 5 below.

TABLE 5

| | Control | 2.0 mM BASS | 1.5 $\mu$M cisplatin | 2.0 mM BASS + 1.5 $\mu$M cisplatin |
| --- | --- | --- | --- | --- |
| Median cell cycle duration (hours) | 19.0 | 21.0 | 41.0 | 58.0 |
| Prolongation (ie cell cycle duration of treated cells | | 1.11 | 2.15 | 3.05 |

TABLE 5-continued

| | Control | 2.0 mM BASS | 1.5 $\mu$M cisplatin | 2.0 mM BASS + 1.5 $\mu$M cisplatin |
| --- | --- | --- | --- | --- |
| relative to control) | | | | |

If the prolongation of 2.0 mM BASS + 1.5 $\mu$M cisplatin had been additive the prolongation due to the drug combination would have been (21/19)×(41/19) or 1.11×2.15=2.39. The prolongation of the combination is 3.05 (i.e. 58/19) which is clearly higher than 2.39, and shows that there is true synergism.

EXPERIMENT 6

This experiment measured, by means of atomic absorption spectroscopy, the amount of cell-associated platinum following 2 hour treatment with 30 $\mu$m cisplatin alone, or 2 hour simultaneous treatment with the combination of 30 $\mu$M cisplatin and either BASS or ascorbic acid. The results are given in Table 6, in which the values given represent the amount of cell associated platinum after the combined treatment relative to that after treatment with cisplatin alone.

TABLE 6

| Concentration of BASS or Ascorbic acid | BASS + 30 $\mu$M cisplatin | Ascorbic acid + 30 $\mu$M cisplatin |
| --- | --- | --- |
| 0 | 1.0 | 1.0 |
| 1 mM | 0.95 ± 0.08 | 0.93 ± 0.09 |
| 2.5 mM | 0.88 ± 0.07 | 0.92 ± 0.06 |
| 5 mM | 0.80 ± 0.06 | 0.85 ± 0.06 |
| 10 mM | 0.76 ± 0.08 | 0.73 ± 0.06 |

Table 6 shows that both BASS and ascorbic acid reduce the relative amount of cisplatin in cells.

Although the experiments described above clearly demonstrate that the use of either BASS or ascorbic acid potentiate the cytotoxic properties of cisplatin, the explanation for the synergistic effects which have been observed is not known. Simple complex formation does not appear to be the answer, since, for example, cisplatin and ascorbic acid do not react to form a complex under the experimental conditions employed.

Although the above experiments utilized either BASS or ascorbic acid and cisplatin, it is to be expected that other derivatives of ascorbic acid would also show similar synergism with cisplatin, or that other anti-cancer platinum complexes such as spiro-platinum and carbo-platinum would also be potentiated by, e.g., BASS or ascorbic acid.

Although the above experiments utilized the sodium salt of 5,6-O-benzylidene-L-ascorbic acid, it is within the scope of the present invention to use other pharmaceutically acceptable salts, in particular other pharmaceutically acceptable alkali and alkaline earth metal salts. The sodium salts are, however, preferred, being well-soluble in water.

Likewise, in some instances it may be preferred to use a pharmaceutically acceptable salt of L-ascorbic acid rather than the free acid itself.

The two active ingredients may be formulated together in a pharmaceutical composition for simultaneous intravenous injection, or alternatively each active ingredient may be administered separately, provided that the patient receives the correct dosage of each active ingredient substantially simultaneously to ensure that the synergistic effect is manifested in the patient.

More particularly, as the accepted route of administration for cisplatin is by intravenous injection as shown in the art of cancer chemotherapy, the BASS or L-ascorbic acid may be given either orally to immediately precede, or simultaneously with, cisplatin administration. For oral administration 5,6-O-benzylidene-L-ascorbic acid or salt thereof, or of a deuterated aldehyde derivative, will be in the range of 10 to 75 mg per kg of body weight up to twice daily, with the anti-cancer platinum compound being given during one of the BASS treatment periods. Acceptable ranges for L-ascorbic acid, or salt thereof, will be from 10 to 100 mg per kq of body weight up to twice daily. For intravenous infusion or injection, BASS or ascorbic acid, or an acceptable salt thereof, may be given simultaneously with but independently of the platinum treatment, or simultaneously with and in admixture with the anti-cancer platinum compound. The suitable ranges for 5,6-O-benzylidene-L-ascorbic acid or alkaline earth salts thereof, or of the deuterated compounds, will be 10 to 75 mg per kg of body weight up to twice daily with the anti-cancer platinum compound being administered during one of the BASS treatment periods. Ascorbic acid as sodium ascorbate or buffered with sodium carbonate will be present in the drug combination regimen at physiologically acceptable levels, normally approximately 10 to 100 mg per kg of body weight up to twice daily with the anti-cancer platinum compound being administered during one the ascorbic acid treatment periods. The dosage of cisplatin or other platinum complex is suitably within the range of 0.5 to 2 mg per kg of body weight for cisplatin, or from 0.5 to 50 mg per kg of body weight for other anti-cancer platinum compounds, for example carboplatinum, either once every 3–4 weeks as a single dose, or daily from 1 to 5 days as split dosages such that the total platinum dosage does not exceed the above ranges.

Thus, for example, for an adult patient, 0.15 g to 1.5 g of BASS or L-ascorbic acid will preferably be given orally per day in combination with up to 150 mg of cisplatin intravenously. For infusion, an adult patient preferably would receive 0.15 g to 1.5 g of BASS or L-ascorbic acid, either in combination with 50 to 150 mg of cisplatin or singly, in the latter case the cisplatin then also being given singly but substantially simultaneously.

Pharmaceutical compositions containing both the active ingredients of the present invention for intravenous infusion or injection may be formulated in numerous ways well known to those skilled in the art with pharmaceutically acceptable excipients or carriers for injection or infusion. As indicated above, freeze-dried mixtures of the active ingredients in a unit dosage form, prepared by conventional methods, preferably are made up with water for injection or other suitable infusion liquid at the time of administration.

The content of the active ingredients in the pharmaceutical compositions according to this invention may vary quite widely, depending on the required dosage. For administration, the content of 5,6-O-benzylidene-L-ascorbic acid or L-ascorbic acid, or pharmaceutically acceptable salt thereof, will usually be about 10:1 to 1000:1 by weight, with respect to the anti-cancer platinum complex present in the composition. Corresponding amounts will apply for the deuterated BASS compounds. Preferably, the compositions will comprise from 5 mg to 500 mg of the anti-cancer platinum complex, and from 100 mg to 10,000 mg of the ascorbic acid or ascorbate. Mannitol and/or sodium chloride may preferably be included in amounts conventional for cisplatin preparations.

Physiological pH of injectables or infusion drug combinations will be established by inclusion of buffering agents as is known in the pharmaceutical art.

For oral administration of L-ascorbic acid or BASS, the compositions containing these active ingredients may be presented in the form of tablets, capsules, granules or powders, in accordance with procedures known in the pharmaceutical formulation art.

We claim:

1. A pharmaceutical composition useful as an agent suitable for the treatment of a cancer sensitive to the composition, said composition comprising an anti-cancer effective amount of a synergistic combination of
   (i) cis-platin, and
   (ii) 5,6-O-benzylidene-L-ascorbic acid or a pharmaceutically acceptable salt thereof and a pharmaceutically acceptable carrier therefor.

2. A composition according to claim 1 wherein said pharmaceutically acceptable salts are selected from alkali metal and alklaine earth metal salts.

3. A composition according to claim 1 wherein the combination of ingredients (i) and (ii) is in freeze dried form.

4. A composition according to claim 3 comprising from 5 mg to 500 mg by weight of (i) and from 100 mg to 10,000 mg of (ii).

5. A composition according to claim 4 which also contains mannitol and sodium chloride.

6. A method for the treatment of cancer in a patient which comprises administering to said patient an anti-cancer effective amount of a synergistic combination of
   (i) cis-platin, and
   (ii) 5,6-O-benzylidene-L-ascorbic acid or a pharmaceutically acceptable salt thereof, the cancer being one sensitive to the combination, the administration of (i) being by injection and the administration of (ii) being by injection or orally.

7. A method according to claim 6 wherein (i) and (ii) are administered simultaneously by injection.

8. A method according to claim 6 wherein (i) and (ii) are separately administered.

9. A method according to claim 6 wherein (i) is administered by infusion in an amount of from 0.05 to 50 mg per Kg of body weight of the patient per day, and in conjunction therewith (ii) is administered in an amount of from 10 to 100 mg per Kg of body weight of the patient.

* * * * *